United States Patent

Jones et al.

[11] Patent Number: 5,999,256
[45] Date of Patent: Dec. 7, 1999

[54] PARTICLE MEASUREMENT SYSTEM

[75] Inventors: Robert Jones; Michael Stuart Hazell, both of Cambridge, United Kingdom

[73] Assignee: Cambridge Consultants Limited, United Kingdom

[21] Appl. No.: 09/055,122

[22] Filed: Apr. 3, 1998

Related U.S. Application Data

[62] Continuation-in-part of application No. 08/589,805, Jan. 22, 1996, abandoned, which is a continuation-in-part of application No. 08/133,055, filed as application No. PCT/GB93/00289, Feb. 11, 1993, abandoned.

[30] Foreign Application Priority Data

Feb. 12, 1992 [GB] United Kingdom .................. 9202887

[51] Int. Cl.⁶ .................................................. G01N 15/02
[52] U.S. Cl. ........................ 356/335; 356/336; 356/338; 356/28
[58] Field of Search ..................... 356/335, 336, 356/338, 341, 342, 28, 309, 318; 250/361, 304

[56] References Cited

U.S. PATENT DOCUMENTS

| | | |
|---|---|---|
| 3,020,792 | 2/1962 | Kingsbury . |
| 3,508,066 | 4/1970 | Agar .......................................... 356/28 |
| 3,519,351 | 7/1970 | Lerwill ....................................... 356/28 |
| 3,819,270 | 6/1974 | Hirschfeld ................................. 356/39 |
| 3,916,197 | 10/1975 | Fulwyler .................................. 356/335 |
| 3,941,479 | 3/1976 | Whitehead .............................. 356/335 |
| 4,514,257 | 4/1985 | Karlsson et al. ........................ 356/335 |
| 4,573,796 | 3/1986 | Martin et al. ............................ 356/343 |
| 4,669,876 | 6/1987 | Dopheide ................................. 356/785 |
| 4,854,705 | 8/1989 | Bachalo .................................. 356/336 |
| 4,893,929 | 1/1990 | Miyamoto ............................... 356/336 |
| 4,923,298 | 5/1990 | Dopheide et al. ......................... 356/28 |
| 4,986,659 | 1/1991 | Bachalo .................................. 356/336 |
| 5,257,087 | 10/1993 | Furuya .................................... 356/335 |
| 5,495,105 | 2/1996 | Nishimura et al. ..................... 356/335 |
| 5,561,515 | 10/1996 | Hairston et al. .......................... 356/28 |

FOREIGN PATENT DOCUMENTS

| | | |
|---|---|---|
| A-0426341 | 8/1991 | European Pat. Off. . |
| A-63-201554 | 8/1988 | Japan . |
| A-2054143 | 11/1981 | United Kingdom . |

OTHER PUBLICATIONS

Patent Abstracts of Japan, vol. 12, No. 488 (p. 803) (3335) Dec. 20, 1988.

*Primary Examiner*—Frank G. Font
*Assistant Examiner*—Layla Lauchman
*Attorney, Agent, or Firm*—Lerner, David, Littenberg, Krumholz & Mentlik, LLP

[57] ABSTRACT

A method for particle size detection comprises passing particles in a fluid medium relative to a light source which generates a light field the optical axis of which is transverse to the direction of fluid movement relative to the said light source and having a plurality of non-interferometrically formed variations in intensity spaced along the direction of movement of the particles relative to the light field, detecting variations in light intensity caused by the particles as they pass through the variations in the light field, and measuring the size of a detected particle substantially independently of the optical characteristics of the particle by plotting the mean peak signal as a function of the normalised peak-to-trough variation in the output pulses generated by the passages of the particle through the light field.

10 Claims, 10 Drawing Sheets

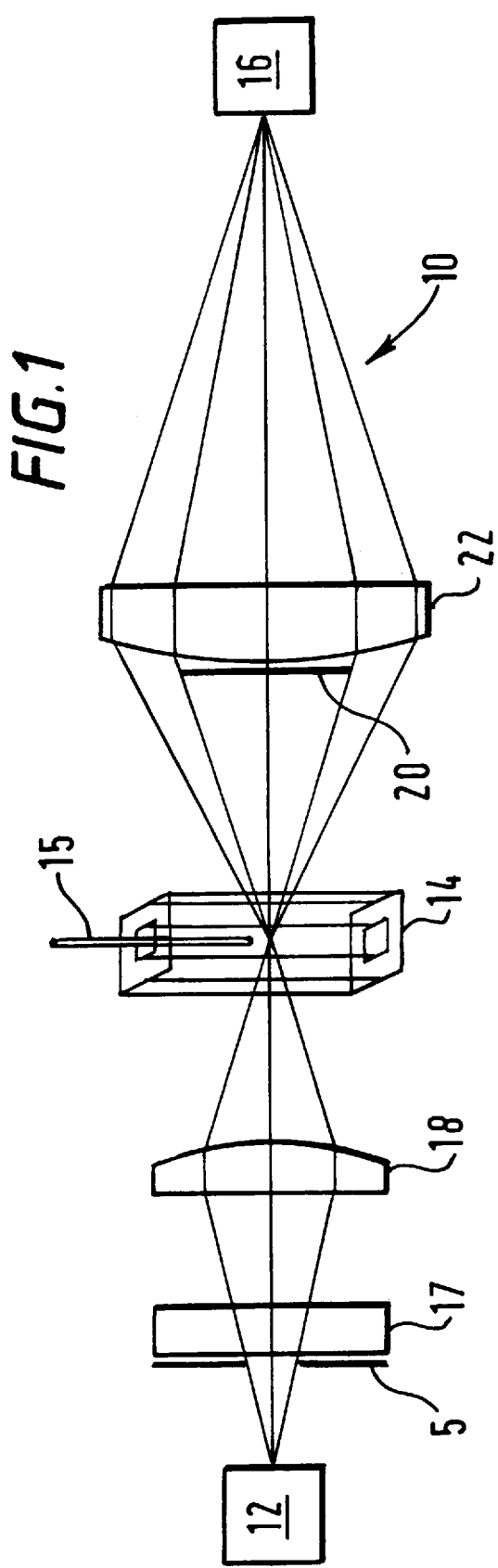
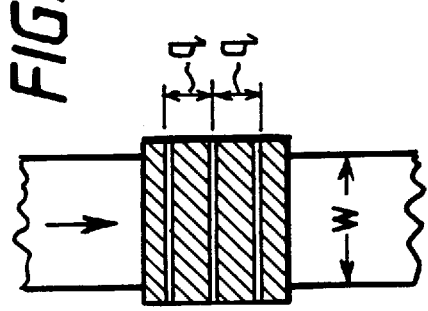

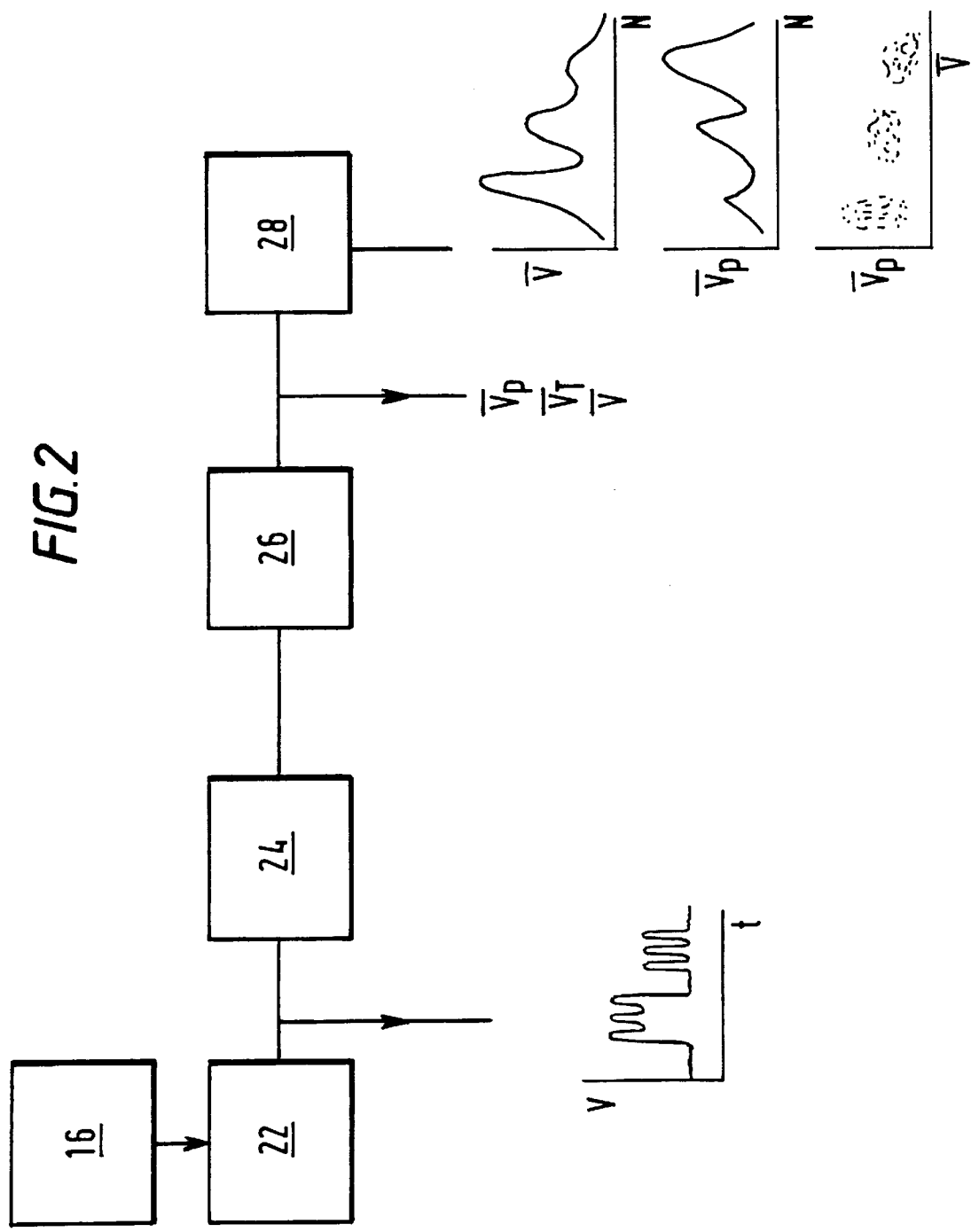

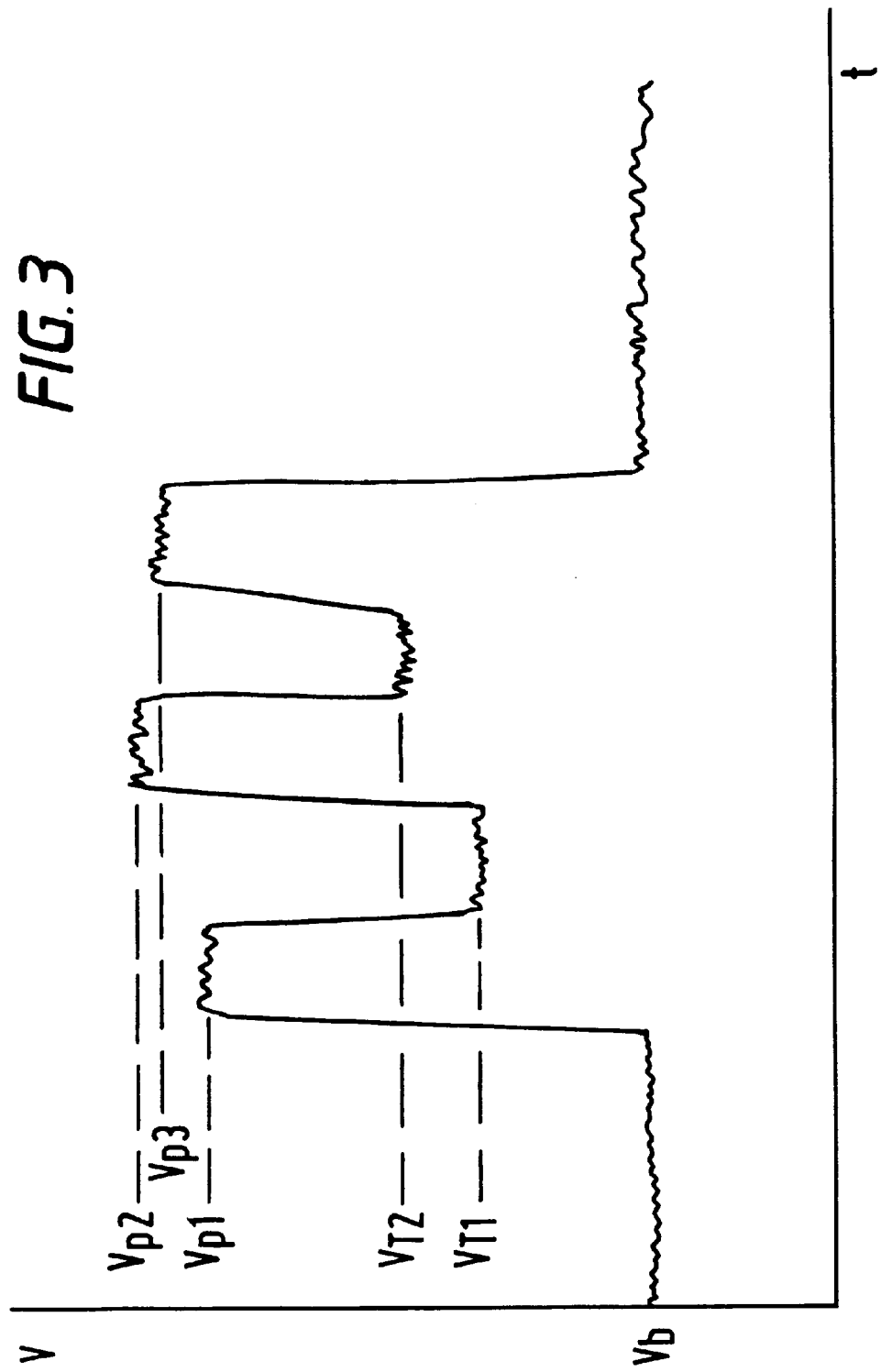

2 × 9 μm particles

5 μm  9 μm

5 μm particle

9 μm particle

3 μm particle

3 μm particle

1 μm particle

1 μm particle

FIG.8a : Obscuration profile of 5μm red blood cell
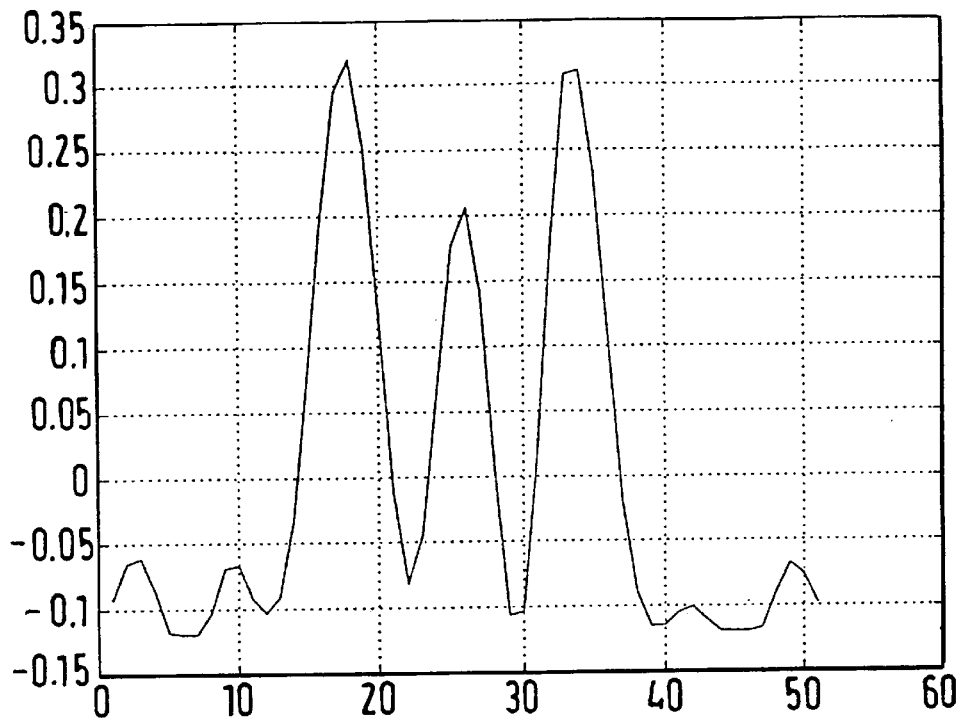
FIG.8b : Obscuration profile of 10μm white blood cell
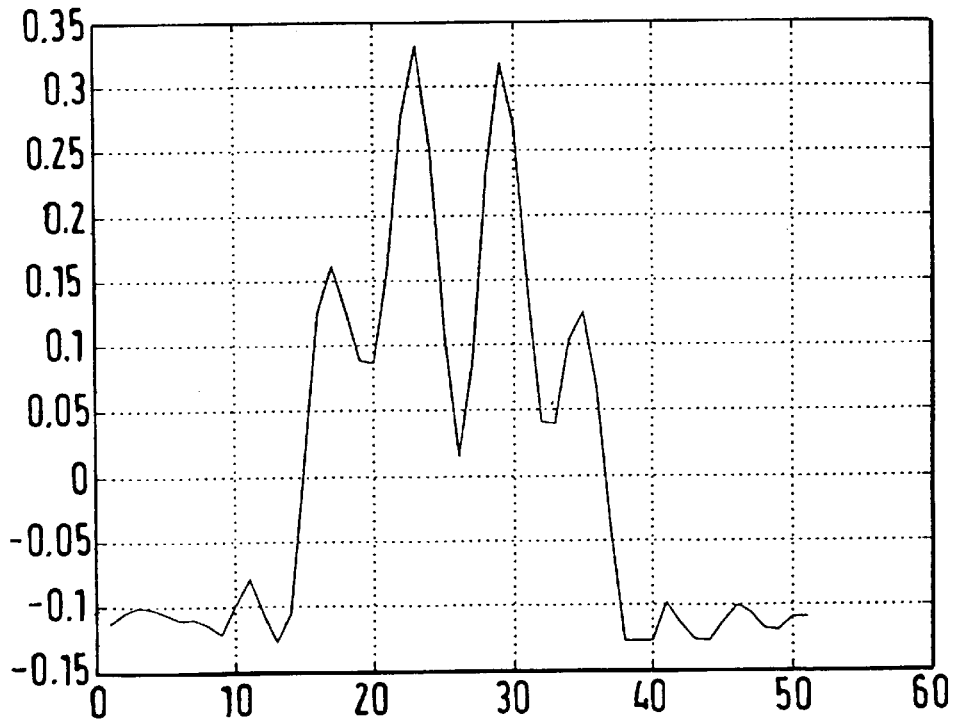

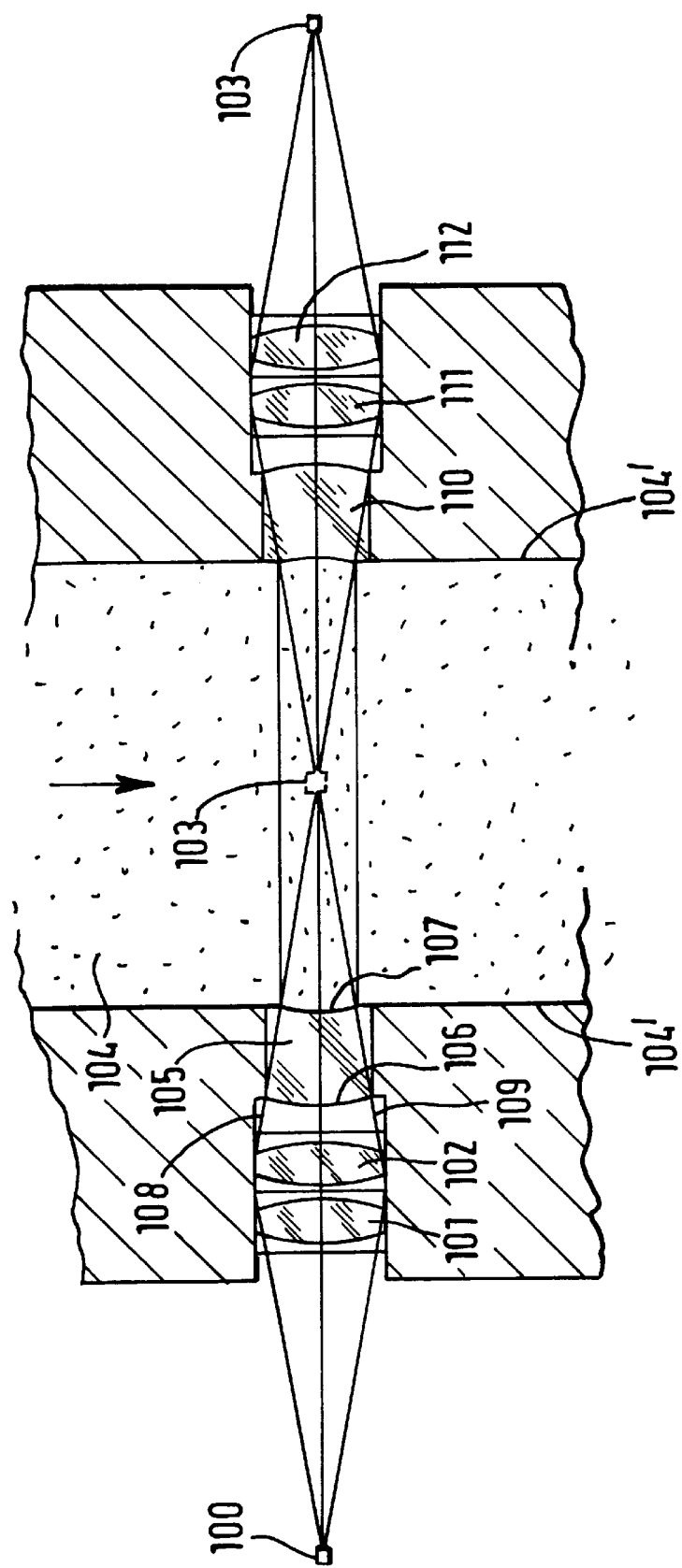

PARTICLE MEASUREMENT SYSTEM

CROSS REFERENCES TO RELATED APPLICATIONS

This application is a continuation-in-part of Ser. No. 08/589,805 (now abandoned) filed on Jan. 22, 1996 which is a continuation-in-part of Ser. No. 08/133,055 filed on Dec. 2, 1993, abandoned, and which was filed as International Application No. PCT/GB93/00289 filed Feb. 11, 1993.

BACKGROUND OF THE INVENTION

Particle sizing by means of optical techniques using Doppler methods which measure the amount of light scattered by the particle as it passes through a light field is widely practised. For biological particles of diameter 1–10 µm and sub-micron particles the scattered light levels are low. Usually therefore particles are made to flow in a focused light field through a flow cell.

Particular sizing techniques based on Doppler methods require the interferometric combination of crossed laser beams to create a structured pattern. This requires the coherent laser light sources and precision lasers, or more recently, the use of diffraction gratings. The extent of the structured light field necessarily occupies a large part of the inspection volume and consequently requires quality optical components. These requirements are not consistent with the manufacture of a low cost particle sizing equipment.

A problem of known techniques that rely purely on scattered light is that the region of focus is frequently subject to significant variations in radiant intensity when it occupies practical sample volumes. A given particle passing through a region of high focal intensity can therefore scatter the same signal as a larger particle in a region of defocus. It has been proposed to overcome this problem by providing a composite light beam incorporating a concentric trigger of one wavelength through the centre of a surrounding analysis beam having a second wavelength. Only particles whose presence is indicated by the trigger beam are analysed. This occurs when the particle traverses the uniform region of the analysis beam. Measurements of the intensity of scattered light are thus made under repeatable conditions of particle illumination. This technique still requires high precision optics however and does not overcome the difficulty that the intensity of light scattered by particles is not a single valued function of the particle size, so that light intensity does not necessarily provide a reliable indication of particle size.

For example in medical bacteria tests in urine, tests for bacteria (typically 1–4 µm) may not clearly be distinguished from residual red cells (5–8 µ) or even white cells (10–15 µm). Additionally still greater expense and complexity is involved.

Thus particle size measurement based solely on the detection of the intensity of the light obscured by a particle as it passes through a uniform focused light field is subject to the major limitation that the signal is a combined function of:

(a) the position of the particle relative to the focal point of the illumination beam (b) the size, refractive index and absorbtion of the particle.

The first of these limitation means that a large particle passing outside of the focus can generate the same amplitude of obscuration as a small particle passing through the focus. This ambiguity is generally overcome in practice by constraining the flow to the region of focus with the result that the system is vulnerable to blockage and unsuitable for a line measurement. Even under these conditions particles of the same size but having either different refractive indices or absorbtion can give different signals.

The present invention is concerned with reducing the above mentioned disadvantages.

SUMMARY OF THE INVENTION

The present invention overcomes the above limitations by analysing the form of the obscuration light signal that results from the particle passing through a focal region in which there exists a cyclic variation in intensity. This means that the light obscured by particles passing outside of the structured focal zone does not carry the modulation envelope generated by particles that pass through the focal zone. Signals in this category are recognised and rejected by the signal processor. A well defined particle sample volume with dimensions equal to the focal zone is thereby defined without the need to constrain the flow and the problems that this introduces.

According to one aspect of the present invention a method for particle detection comprises passing particles in a fluid medium relative to a light source which generates a light field the optical axis of which is transverse to the direction of fluid movement relative to the said light source and having a plurality of non-interferometrically formed variations in intensity spaced along the direction of movement of the particles relative to the light field, detecting variations in light intensity caused by the particles as they pass through the variations in the light field, and measuring the size of a detected particle substantially independently of the optical characteristics of the particle by plotting the mean peak signal as a function of the normalised peak-to-trough variation in the output pulses generated by the passages of the particle through the light field.

According to a second aspect the present invention comprises apparatus for particle measurement comprising apparatus for measuring particles comprising a light source for generating a light field having a plurality of spaced variations in intensity, means for moving particles in a fluid medium relative to the light field so that the particles pass successively through the intensity variations, and means for detecting variations in light intensity caused by the passage of the particle relative to the light field.

BRIEF DESCRIPTION OF THE DRAWINGS

Various embodiments of the invention will now be described by way of example and with reference to the following drawings in which:

FIGS. 1 and 1A illustrate the layout of optical components in one form of particle sizer according to the invention;

FIG. 2 is a block diagram of a typical signal processing system for the analysis of a particle size distribution based on signals from the light detector of FIG. 1;

FIG. 3 shows a general form of an output signal generated by the embodiment of FIG. 1;

FIGS. 8A and 8B show two different obscuration profiles; and

FIG. 9 show another embodiment of the light detection optics system.

Referring now to FIG. 1 of the accompanying drawings this shows the optical layout of one embodiment of apparatus according to the present invention for sizing particles in a fluid stream and is generally indicated at 10 for sizing particles in a fluid stream. A potential application of the apparatus is to detect the presence of bacteria in urine. However it will be appreciated that the apparatus could also be used in a similar manner to measure particles carried in a gaseous medium, and that the term "fluid medium" as used in the present specification is intended to cover both gaseous and liquid media.

Figure 4A:
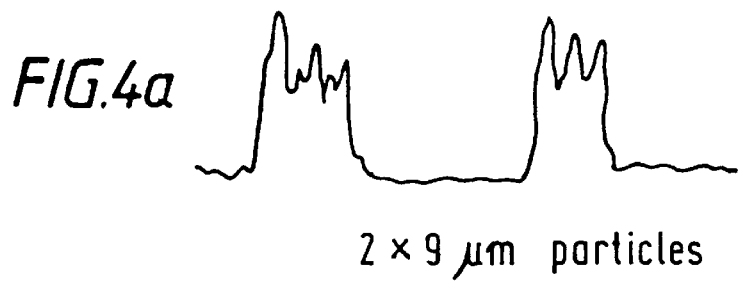
FIG. 4(a)–4(f) shows experimental results of the voltage output signal from the detector of the embodiment of FIG. 1.
Figure 4B:
Figure 4C:
Figure 4D:
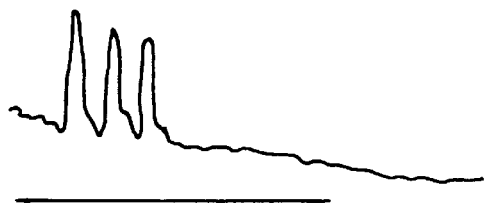
Figure 4E:
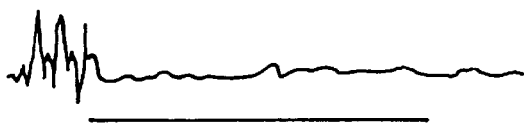
Figure 4F:
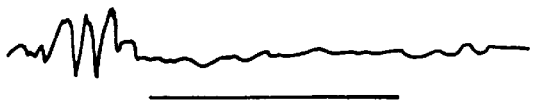

The apparatus 10 comprises a light source 12, a flow cell 14 and a light detector 16.

The light source 12 is a structured light source comprising an array of discrete light emitting elements uniformly separated. In a preferred form the structured light source 12 is realised by laser diodes having multiple facets. The source illustrated comprises three facets, but may in practice incorporate any suitable number of uniformly separated emitting elements.

The light source 12 is imaged by the aperture 5 and cylindrical lenses 17 and 18 into the inspection volume of the flow cell 14. In the preferred embodiment of the invention the structured light source comprises a laser diode, e.g. Sharp type LTO90MFO(TM) in which the three light emitting facets are strips approximately 3 microns by 1 micron and separated by 50 microns. For the detection of *E. coelli* in urine the magnification of the lens systems 17 and 18 is chosen so that the separation of the intensity peaks in the focused image is approximately 5 microns. Thus in the embodiment being described the actual volume of fluid in the effective area of light is approximately 20×20×20 microns to 200×200×200 microns. When it is required to sample the particle population the fluid under test may be passed through a standard flow cell or piping of non-critical dimensions. If it is necessary to measure all the particles present it is preferred to inject a stream of fluid into cell 14 by means of a narrow bore pipe 15 such as a hypodermic needle so that the particle stream passes entirely through the focused light or to limit the flow cell dimensions of those of the focal region. In these latter cases the scale of the flow region is typically in the range of 20 to 200 microns dependent on the optical configuration. The fluid can be supplied under gravity or by a suitable pump.

FIG. 1a shows a stream of fluid passing through the three focused facets of the light source 12. As shown in FIG. 1a the image of the line source facets section the flow cell normal to the flow direction and extend beyond the width (w) of the flow cell. The depth of focus is made equal to that of the cell when it is required to measure every particle. The sample volume is defined by the focal region volume when the flow depth is greater than the focal depth. The magnification of the cylindrical lenses is also chosen so that the separation (q) of the image bars or lines approximate to the range of particle size to be measured.

Light from the image volume in the flow cell is collected by lens 22 into the detector 16. A stop 20 is sized so that normally in the absence of particles or other scattering sites in the image column the detector 16 is not illuminated, whilst forward scattered light is collected and detected. The detector 16 can be a PIN diode or an avalanche photo-diode or other suitable photoelectric device.

Particles that traverse the focused light field are thus exposed to light from each facet or focused variation in light intensity in turn. The intensity of light detected is thus modulated with a frequency U/q, where U is the particle traverse velocity and with intensity given by the convolution of the particle scattering cross section with the structured light image. A particle p of diameter D where D>>q effectively smears out the structure and an event of uniform intensity is displayed.

Particles for which D<q partially resolve the structure and thus partially modulate the signal intensity and particles for which D<<q fully resolve the structure and display full modulation with intensity limited only by the detection noise limit.

It will be appreciated that the embodiment being described is capable of measuring bacterial particles which are poor absorbers of light. If the apparatus is intended to measure particles which are good light absorbers then a simple obscuration method could be employed. In such a case the stop 20 could be omitted so that the output of detector 16 would normally be high and the passage of particles through the inspection volume would cause appropriate reductions in the measured light input. However with poorly absorbent particles the signals caused by particle obstruction are small compared to the noise level of the light sensor generated by the directly incident radiation and it is for this reason that a system which detects scattered light is preferred.

The processing of the output signal will now be described by reference to the block diagram illustrated in FIG. 2.

When a particle traverses the inspection volume of the flow cell light scattered in the structured light field by the particle is collected in the detector 16 to generate an output signal which is amplified by an amplifier 22, thresholded by a threshold circuit 24, sampled by an Analogue-to-Digital convertor 24 and analysed by a suitable microprocessor unit 26. A display unit is shown at 28 for displaying the results of the analysis and can take a wide number of different formats such as a CRT-based video system or hard copy device such as a plotter, whilst the microprocessor unit can be a PC.

A general form of the output signal 16 generated by the passage of a single particle is shown in FIG. 3.

Considering this general form of signal the A-D detector typically generates samples from which mean values of the background voltage $V_b$, a set of three peak voltages $V_{p1}$ $V_{p2}$ and $V_{p3}$ corresponding to each facet of the light source structure and two trough voltages $V_{T1}$, and $V_{T2}$ are generated.

System noise in general varies even during the period of a single pulse, as will be apparent from the experimental results illustrated in FIG. 4(a)–(f), generally due to thermal and flow effects.

Accordingly values of the mean peak voltages $V_p$ and trough voltages $V_p$ are corrected for the background voltage value by subtracting the latter as is shown in the following equations.

$$V_{pn}'=V_{pn}-V_b$$

$$V_{tn}'=V_{tn}-V_b$$

Further calculations for each particle sampled are then performed $$\overline{V}_p = \frac{1}{3} \sum_{n=1}^{3} V_{pn}$$

$$\overline{V}_T = \frac{1}{2} \sum_{n=1}^{3} V_n$$

and the visibility V is then calculated $$\overline{V} = \left( \frac{\overline{V}_n - \overline{V}_T}{\overline{V}_n + \overline{V}_T} \right)$$

Figure 5:
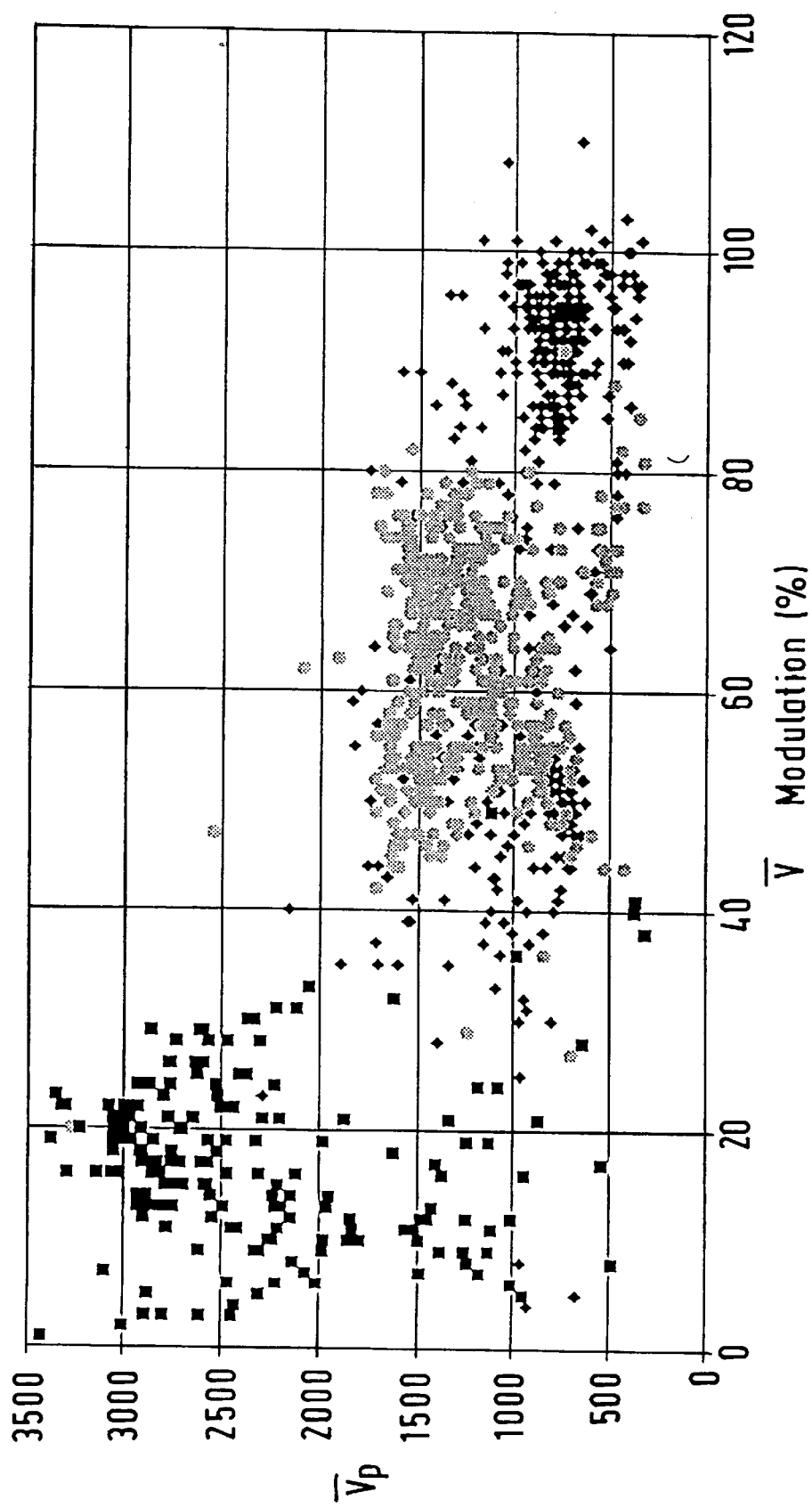
FIG. 5 shows a scatter plot derived from structured outputs showing distribution of particles in the range 9 u to 3 µm.

FIG. 5 shows particularly clearly the effect of this calculation of the normalised peak-to-trough variation. Thus the layer, i.e. 9 $\mu$m particles shown in the left hand side of the figure are particles which have displayed the highest mean peak scatter level and smallest depth of modulation as defined by the mean visibility of the signal. Similarly the smallest, i.e. 3 $\mu$m particles which occupy the bulk of the right hand side of the figure display the lowest mean peak scatter level and highest depth of modulation.

Evidently for a source having a greater number of facets than 3, corresponding summations for the greater number of peak and trough events can be performed. These calculations are carried out in microprocessor unit 26 and the results displayed at 28. The particle size can be collected and displayed in histogram form or in other suitable form of display to illustrate the sizes of particles present. In general the visibility is found to be a single valued function of the particle size, and calibration of the particle sizing instrument is therefore simplified.

FIG. 5 shows a scatter plot from experimental results for particles of 9 $\mu$m, 5 $\mu$m and 3 $\mu$m diameters.

The detection optics illustrated in FIG. 1 places the detector 16 under dark field illumination when there is no particle present in the inspection volume, due to the stop 20. This has the advantage that the scattered light signal can be focused into a small area detector and all the light collected is employed to generate the output signal, thereby minimizing noise. However as already mentioned the stop may be removed, thereby normally exposing the detector 15 to continuous light illumination. When a particle passes through the inspection volume it partly shadows the detector, lowering the illumination. In that case the signal of FIG. 3 is in effect inverted, so that $V_p$ and $V_T$ are lower than $V_b$. However the same calculation is performed to extract the visibility and thus the size of the particle. It is normally to be expected however that the noise component of this arrangement is greater than that described above, so that the accuracy of particle size denomination is lower and the least particle size that can be detected greater. The system without stop 20 in as accordingly less practicable where the particles to be measured have poor light absorbtion characteristics, such as bacteria and blood cells.

Alternative systems for collecting and detecting the. scattered light are illustrated by reference to FIG. 6, in each case using forward scatter. Alternatively it is perfectly feasible to use either side or back scattered light and in fact the actual geometry chosen may be dictated by the practical constraints of the application.

Figure 6A:
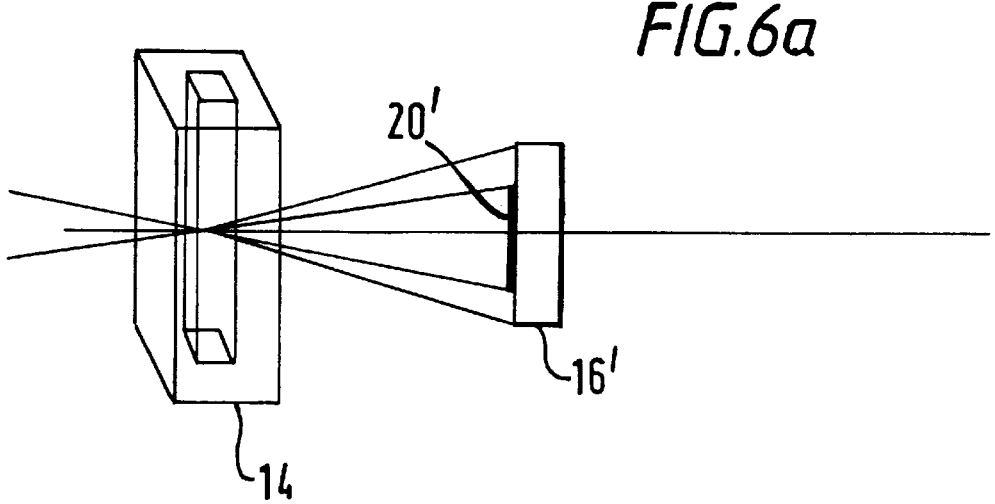
FIGS. 6A and 6B show alternative embodiments of light detection optics systems.
Figure 6B:
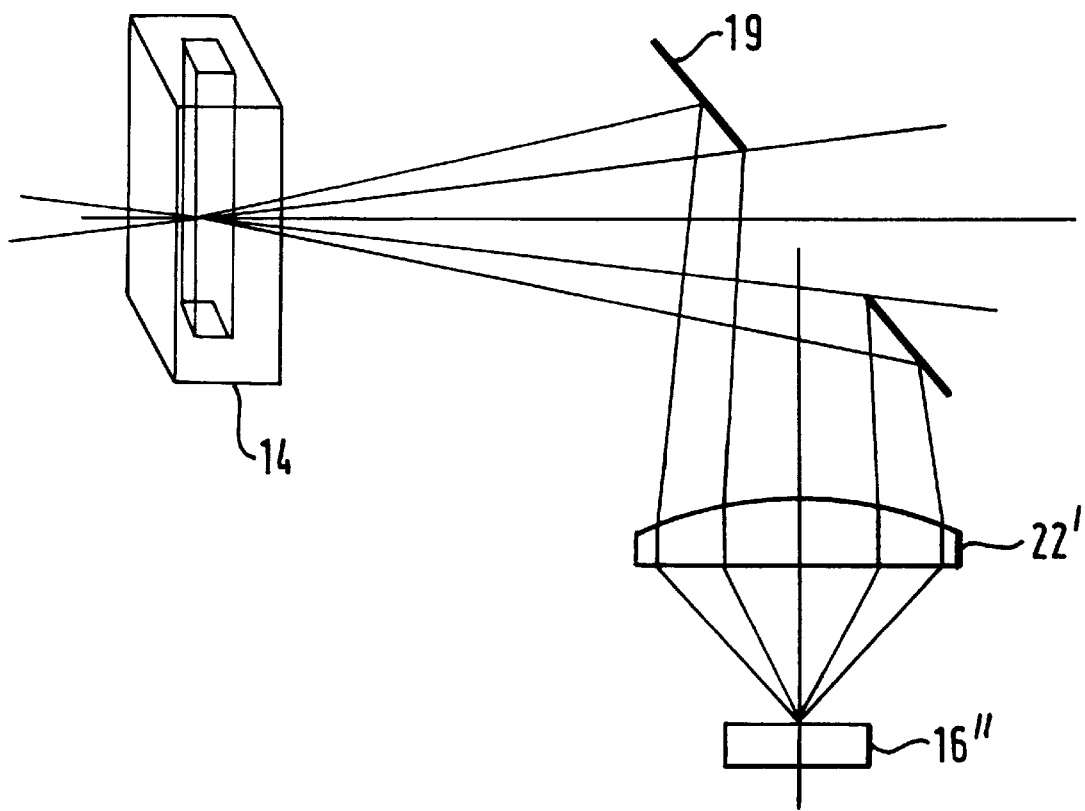

One alternative light collection system in FIG. 6(a) comprises a detector 16' partially screened by stop 20' placed adjacent to the flow cell 14. In this case the detector collects the light without the benefit of a collection lens 22, and consequently the detector is somewhat larger in area. Such an arrangement may be built at less cost, but owing to the larger detection area is subject to increased noise in the detection circuit.

A more compact arrangement is also obtained by incorporating the mirror 19 as well as lens 22'.

Alternatively the mirror 19 can be appropriately curved so that it also acts as a lens so as to provide a simple component which collects and focuses scattered light from the flow cell 14.

In the prior art the structured light field has been generated interferometrically in the form of fringes by focusing light from a coherent laser source via two paths into the inspection volume. In the present invention a structured light field is developed using incoherent methods and may take a number of forms. One convenient form described above takes the form of a multi-faceted light emitting or laser diode which is focused into the inspection volume by means of suitable cylindrical lenses or an equivalent optical system.

However it will be evident that in general the source may be comprised of a number of structurally separate light sources optically combined by suitable beam splitters and cylindrical lenses to provide an equivalent structured image in the inspection volume; or alternatively may be obtained by an array of slits exposing a common light source suitably focused into the image plane; or alternatively may be obtained from a line source divided by a prism (or prisms) or diffraction grating into two or more line sources: and any other structured light field developed using incoherent imaging methods. The objective of the invention is to develop a structured light field having two or more basis of focused light having a predetermined separation (q) having a low manufacturing cost but providing high light intensity.

Figure 7A:
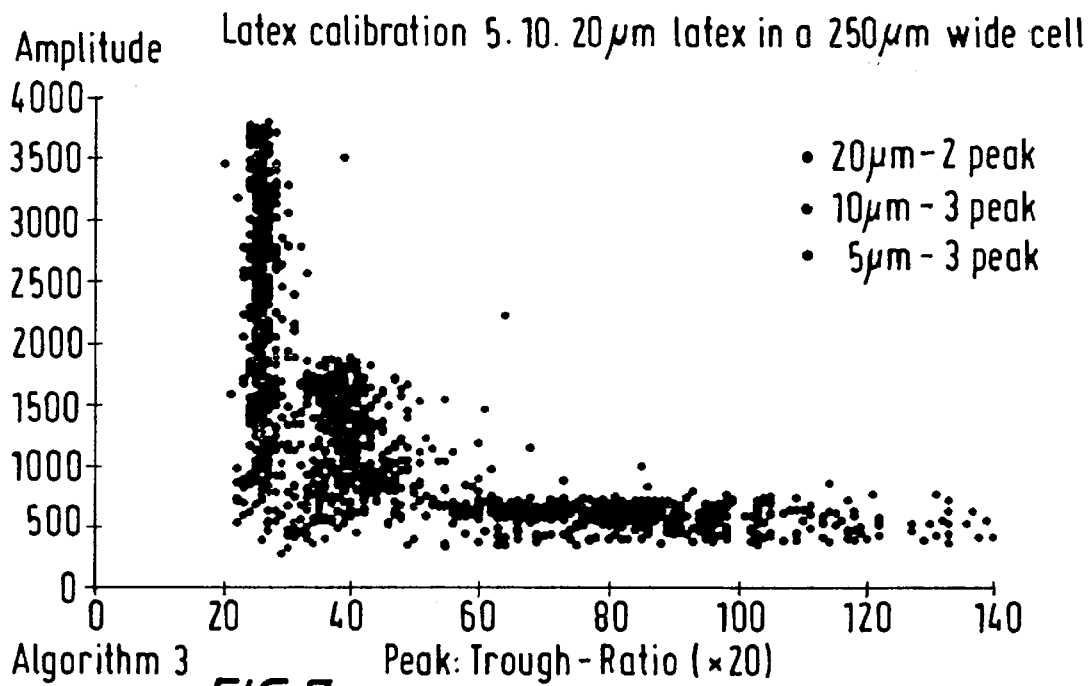
FIGS. 7A and 7B show scatter plots obtained for different cell depths.
Figure 7B:
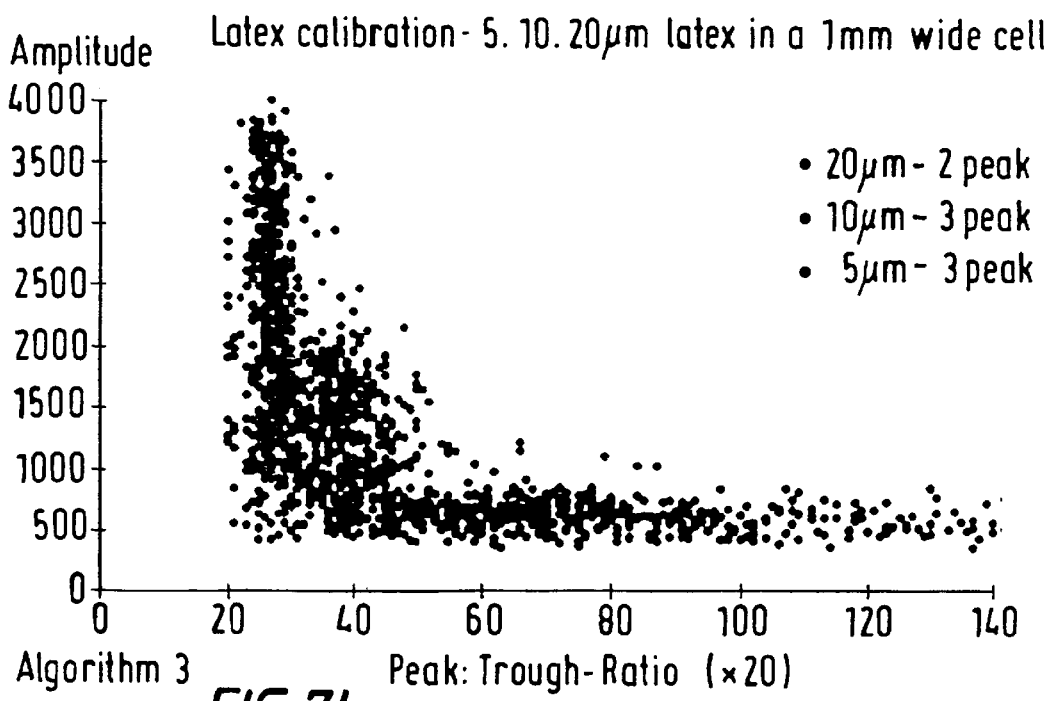

This is illuminated by the experimental results shown in FIGS. 7A and 7B. These show the particle distributions for 5 $\mu$m, 10 $\mu$m and 20 $\mu$m latex spheres in which the mean obscuration signal is plotted against the normalised modulation depth as described in the present specification. The distribution in FIG. 7A was observed for a flow cell depth of 250 $\mu$m which equalled that of the focal region and in which all particles were therefore constrained to pass through the cyclic intensity distribution. The distribution in FIG. 7B was observed for the same flow and particle sizes but with a flow cell of depth 1 mm i.e. nominally four times greater than the sample depth. Note that a distribution almost identical to that in FIG. 7A is observed hence demonstrating the ability to measure particle size distribution under conditions where the fluid flow is not constrained to the focal region.

Referring now to FIG. 9 of the accompanying drawings this figure shows an embodiment of the optical sensing system suitable for use in relatively wide channels through which particles to be measured can flow. In this embodiment the measurement volume in which the cyclically structural light pattern generated by the structural light source and lens system is not in any way defined by the boundaries of the fluid flow channel but purely by optical means.

The FIG. 9 embodiment comprises a structural light source 100 similar to light source 12 sends monochromatic light through a pair of lenses 101, 102 which focus the beam onto a volume generally indicated at 103 in such a manner that at least 3 cyclical and non-interferometrical variations in light intensity are formed transverse to the path of flow through a channel indicated at 104. In order to compensate for possible changes in the refractive index in the fluid flowing in channel 104 the light from lenses 101, 102 passes through a window 105, preferably of glass which has curved faces 106, 107. The curvature of these faces is selected so that the outermost light beams, indicated at 108, 109 enter the fluid at normals to the window surface. Thus the face 107 of the window is curved with a radius equivalent to the distance between the face and the mid point of the channel.

It will be seen that the light leaves the flow channel via a window 110 identical to window 105 where the light passes through a pair of focusing lenses 111, 112 to be detected by a photodetector 113 similar to the detector 16 of FIG. 1. It will be appreciated that the output of detector 113 is processed in a manner similar to the output of detector 16. The fluid flowing in the channel 104 can be gas or liquid. In one embodiment the arrangement shown in FIG. 9 can be used to detect the presence of particles in high pressure oil. It is for the reason of robustness that the windows 105, 110 are shown so thick. The walls 104' can be of any suitable material appropriate to the nature of the fluid flowing in the channel. Naturally the cross-section of the channel has no effect on the actual measurement volume 103.

It is also important to note that the geometrical form of the modulation of the scatter signal (as given by the convolution of the particle cross section with the cyclic intensity distribution) is a sensitive function of the particle size which is independent of the optical characteristics such as refractive index and absorbtion of the particle. This is illustrated in FIGS. 8A and 8B which correspond to the obscuration signals obtained for 5 μm red blood cells and 10 μm white blood cells respectively. The size of the cells may be determined from the readily distinguishable form of the signals irrespective of the fact that the two types of cell have inherently different optical properties.

Although the invention has been described above with regard to particle size measurement it will be evident that the particle speed may also be extracted by monitoring the frequency of the voltage signals obtained. Additionally particle speed in more than one direction can be measured by having a second structured light field and associated optical system. In such a case the facets of the second field could be orthogonal with respect to those of the first field. It will also be appreciated that apparatus of the types just described could be cascaded along the path of particle flow with the facets being separated by varying distances.

We claim:

1. A particle size measurement method comprising passing particles in a fluid medium relative to a monochromatic light source which generates a light field the optical axis of which is transverse to the direction of fluid movement relative to the said light source and having a plurality of cyclical and non-interferometrically formed variations in intensity of the same chromaticity as the light source spaced along the direction of movement of the particles relative to the light field the widths of the cyclical valuations being in accordance with the expected range of size of the particles to be detected, detecting variations in light intensity caused by the particles as they pass through the cyclical variations in the light field, and measuring the size of a detected particle substantially independently of the optical characteristics of the particle by plotting the mean peak signal as a function of the normalised peak-to-trough variation in the output pulses generated by the passages of the particle through the light field.

2. A method according to claim 1, wherein the light source generates three variations in intensity through which each particle successively passes to generate pulses caused by the particle obscuring the light in the light field.

3. Apparatus for measuring the size of particles comprising a light source for generating a monochromatic light field having a plurality of cyclical and non-interferometrically formed spaced variations in intensity of the same chromaticity as the light source the width of the cyclical variation being in accordance with the expected range of size of the particles to be detected; means for moving particles in a fluid medium through to the light field so that the particles pass successively through and transversely with respect to said cyclically spaced variations in intensity, means for detecting variations in light intensity caused by passage of the particles relative to the light field, and means for calculating the size of a particle independently of the optical characteristics of the particle by plotting the mean peak signal as a function of the normalised peak-to-trough variation in the output pulses generated by the passages of the particle through the light field.

4. Apparatus according to claim 3, wherein the means for moving the particles include a conduit adapted to transport a fluid in which the particles are carried, and wherein the light source and the means for detecting are located on either side of said conduit.

5. Apparatus as claimed in claim 4, wherein the light source generates a light field having three spaced variations in intensity.

6. Apparatus as claimed in claim 4, wherein the light source comprises three spaced sources of light generating three parallel beams which extend transverse to the direction of movement of the particles under measurement.

7. Apparatus according to claim 6, and including at least one lens arranged to focus light from the light source into the light field so that the spacing between the variations in intensity is approximately equal to the expected size of a particle to be measured.

8. Apparatus as claimed in claim 4 in which the conduit is a pipe having a diameter between approximately 100 and 300 microns.

9. Apparatus as claimed in claim 4 and including a stop, to prevent direct illumination of the detecting means, the stop being provided adjacent the light detector so that active area of the light detector only receives light scattered by particles.

10. Apparatus according to claim 4, comprising channel means defining a channel through which said medium flows; window means mounted in said channel means and located in the optical path between said light source and means for detecting, and wherein each said window has a curved face the radius of curvature of which corresponds substantially to the distance from the face to the mid point of said channel.

* * * * *

UNITED STATES PATENT AND TRADEMARK OFFICE
CERTIFICATE OF CORRECTION

PATENT NO. : 5,999,256
DATED : December 7, 1999
INVENTOR(S) : Robert Jones, Michael Stuart Hazell It is certified that error appears in the above-identified patent and that said Letters Patent is hereby corrected as shown below:

Column 1, Lns. 3-5, before CROSS REFERENCES TO RELATED APPLICATIONS, please insert:

-- The present invention relates to the optical measurement of particles and particularly, though not exclusively, to the measurement of particle sizes. --

Column 3 Ln. 7, "(5-8μ)" should read -- (5-8 μm) --.

Column 8 Ln. 8, "5" should read -- 15 --.

Column 12 Ln. 22, "$V_{pn}$" should read -- $V_{pn'}$ --.

Column 12 Ln. 23, "$V_m$" should read -- $V_{tn'}$ --.

Column 13 Ln. 2, "$V_n$" should read -- $V_{pn}$ --.

Signed and Sealed this

Twenty-fourth Day of April, 2001

Attest:

NICHOLAS P. GODICI

Attesting Officer

Acting Director of the United States Patent and Trademark Office